(12) United States Patent
Jangle et al.

(10) Patent No.: US 8,972,197 B2
(45) Date of Patent: Mar. 3, 2015

(54) METHOD AND SYSTEM FOR ANALYZING BREATHING OF A USER

(75) Inventors: Jeetendra Jangle, Fremont, CA (US); Umang Salgia, Pune (IN); Rajendra Sapre, Pune (IN)

(73) Assignee: Numera, Inc., Seattle, WA (US)

( * ) Notice: Subject to any disclaimer, the term of this patent is extended or adjusted under 35 U.S.C. 154(b) by 1193 days.

(21) Appl. No.: 12/891,108

(22) Filed: Sep. 27, 2010

(65) Prior Publication Data

US 2011/0066064 A1    Mar. 17, 2011

Related U.S. Application Data

(63) Continuation-in-part of application No. 12/560,069, filed on Sep. 15, 2009, now abandoned.

(51) Int. Cl.
| | |
|---|---|
| G01N 33/48 | (2006.01) |
| A61B 5/00 | (2006.01) |
| A61B 5/08 | (2006.01) |
| A61B 5/113 | (2006.01) |
| G06K 9/00 | (2006.01) |
| A61B 5/0205 | (2006.01) |
| A61B 5/0402 | (2006.01) |

(52) U.S. Cl.
CPC ............. *A61B 5/7214* (2013.01); *A61B 5/0816* (2013.01); *A61B 5/113* (2013.01); *A61B 5/6822* (2013.01); *A61B 5/6831* (2013.01); *G06K 9/00342* (2013.01); *A61B 5/0205* (2013.01); *A61B 5/0402* (2013.01); *A61B 5/726* (2013.01)
USPC .......................................................... 702/19

(58) Field of Classification Search
CPC ................. A61M 2206/10; A61M 2016/0027; A61M 2205/50
See application file for complete search history.

(56) References Cited

U.S. PATENT DOCUMENTS

| | | | |
|---|---|---|---|
| 4,307,728 A | * | 12/1981 | Walton .......................... 600/500 |
| 4,513,437 A | | 4/1985 | Chainer et al. |
| 6,028,626 A | | 2/2000 | Aviv |
| 6,160,478 A | | 12/2000 | Jacobsen et al. |
| 6,166,639 A | | 12/2000 | Pierce et al. |
| 6,626,728 B2 | | 9/2003 | Holt |
| 6,675,649 B2 | | 1/2004 | Uchiyama et al. |
| 6,756,889 B2 | | 6/2004 | Sala et al. |
| 6,802,814 B2 | | 10/2004 | Narimatsu |
| 6,816,766 B2 | | 11/2004 | Sala et al. |
| RE38,729 E | | 4/2005 | Liu |
| 6,999,863 B2 | | 2/2006 | Neal et al. |
| 7,145,461 B2 | | 12/2006 | Lehrmann et al. |
| 7,248,172 B2 | | 7/2007 | Clifford et al. |

(Continued)

OTHER PUBLICATIONS

Response to Office Action submitted Jan. 23, 2011, for U.S. Appl. No. 12/560,069, filed Sep. 15, 2009.

(Continued)

*Primary Examiner* — Elias Desta
(74) *Attorney, Agent, or Firm* — Brian R. Short

(57) ABSTRACT

Methods, systems and apparatus for analyzing breathing of a user are disclosed. One method includes sensing motion of a first portion of the user, sensing motion of a second portion of the user, and generating a summed signal by inversely summing the sensed motion of the first portion of the user with the sensed motion of the second portion of the user. A breathing rate of the user is estimated based on the summed signal. Additionally, a breathing pattern of the user can be identified.

24 Claims, 11 Drawing Sheets

(56) References Cited

U.S. PATENT DOCUMENTS

| | | |
|---|---|---|
| 7,467,060 B2 | 12/2008 | Kulach et al. |
| 7,715,982 B2 | 5/2010 | Grenfell et al. |
| 7,827,000 B2 | 11/2010 | Stirling et al. |
| 8,060,337 B2 | 11/2011 | Kulach et al. |
| 2003/0158489 A1 | 8/2003 | Narimatsu |
| 2005/0154512 A1 | 7/2005 | Schubert et al. |
| 2006/0005578 A1 | 1/2006 | Tortoli |
| 2006/0089538 A1 | 4/2006 | Cuddihy et al. |
| 2006/0282021 A1 | 12/2006 | DeVaul et al. |
| 2007/0167693 A1 | 7/2007 | Scholler et al. |
| 2007/0293781 A1 | 12/2007 | Sims et al. |
| 2008/0214903 A1 * | 9/2008 | Orbach .................. 600/301 |
| 2008/0256796 A1 | 10/2008 | Fix |
| 2008/0262381 A1 | 10/2008 | Kolen |
| 2009/0303204 A1 | 12/2009 | Nasiri et al. |
| 2010/0073284 A1 | 3/2010 | Dods et al. |
| 2010/0121226 A1 | 5/2010 | Ten Kate et al. |
| 2010/0137730 A1 | 6/2010 | Hatlestad |
| 2010/0168599 A1 | 7/2010 | Esposito et al. |
| 2010/0217533 A1 | 8/2010 | Nadkarni et al. |
| 2010/0240945 A1 | 9/2010 | Bikko |

OTHER PUBLICATIONS

Response to Office Action submitted Apr. 2, 2013, for U.S. Appl. No. 12/621,099, filed Nov. 18, 2009.

Response to Office Action submitted May 10, 2012, for U.S. Appl. No. 12/883,304, filed Sep. 16, 2010.

* cited by examiner

Breathing Pattern for Deep Breathing

Breathing Pattern for Normal Breathing

Breathing Pattern for Slow Inhale, Fast Exhale

Breathing Pattern for Shortness of Breath

METHOD AND SYSTEM FOR ANALYZING BREATHING OF A USER

RELATED APPLICATIONS

This patent application is a continuation in part (CIP) of U.S. patent application Ser. No. 12/560,069 filed on Sep. 15, 2009, which is incorporated by reference.

FIELD OF THE DESCRIBED EMBODIMENTS

The described embodiments relate generally to monitoring health of a user. More particularly, the described embodiments relate to a method, system and apparatus for monitoring breathing of a user while the user is in motion.

BACKGROUND

There is an increasing need for remote monitoring of individuals, animals and inanimate objects in their daily or natural habitats. Many seniors live independently and need to have their safety and wellness tracked. A large percentage of society is fitness conscious, and desire to have, for example, workouts and exercise regimen assessed. Public safety officers, such as police and firemen, encounter hazardous situations on a frequent basis, and need their movements, activities and location to be mapped out precisely.

Of particular importance is the breathing rate and breathing pattern of a user. Monitoring of breathing is particularly useful because it helps, for example, in identifying progress and effectiveness of an exercise regime. During aerobic activities like running, and cycling, a good steady breathing pattern ensures that muscles are getting enough nourishment in terms of oxygen so that they can perform optimally without injury. It is also possible to determine the intensity of the exercise based on the breathing patterns of the person. Change in respiration rate and pattern is also known to be the earliest indicator of physiological instability, organ distress, health problems, and onset of chronic conditions. Training in the use of proper breathing rates and patterns, have proven to cure the persons of many chronic conditions and significant reduction of stress.

Present breathing devices require the user to be stationary. However, the breathing monitoring is particularly useful when the user is non-stationary. Demand for oxygen goes up in non-stationary conditions exercising, such as running. Improper breathing retards metabolic energy production. This can lead to fatigue and result in muscle and body injuries. Proper breathing improves oxygen concentration at the cellular level. It has also been shown that ensuring better breathing patterns can immediately increase the energy level in the body. Public safety officers, such as, firemen can be exposed to hazardous conditions of smoke and deadly chemicals while trying to fight the fires. It is imperative that they be monitored for their safety while they are moving. As a part of their training, firemen are taught to breathe in such conditions. Monitoring of their breathing helps to ensure that they can be evacuated from a site before they reach critical condition due to exposure to smoke, poisonous gases and chemicals.

Existing products for the detection of human motions are simplistic in nature, and incapable of interpreting anything more than simple atomic movements, such as jolts, changes in orientation and the like. It is not possible to draw reliable conclusions about human behavior from these simplistic assessments.

It is desirable to have an apparatuses, systems and methods for monitoring breathing of a user. In is particularly desirable to monitor the breathing of the user while the user is active.

SUMMARY

An embodiment includes a method of analyzing breathing of a user. The method includes sensing motion of a first portion of the user, sensing motion of a second portion of the user, and generating a summed signal by inversely summing the sensed motion of the second portion of the user with the sensed motion of the first portion of the user. A breathing rate of the user is estimated based on the summed signal.

Another embodiment includes a system for converting or reconstructing the signal from the first part as if it were taken from the second part of the body, such that it accurately estimates the signal generated by the motion experienced at the second part, excluding any signal captured due to breathing.

Another embodiment includes a method for indentifying a type of breathing pattern of a person. The method includes generating an acceleration signature based on the sensed acceleration of a motion sensing device attached to the person. The acceleration signature is matched with at least one of a plurality of stored acceleration signatures, wherein each stored acceleration signature corresponds with a type of breathing pattern. The type of breathing pattern is identified based on the statistical matching or exact matching of the acceleration signature.

Another embodiment includes an apparatus for analyzing the breath rate and the breathing patterns. If the breathing rate and pattern are outside of normal range for the kind and intensity of activity being performed and if it reaches a health risk zone, the apparatus is capable of sending an alert.

Other aspects and advantages of the described embodiments will become apparent from the following detailed description, taken in conjunction with the accompanying drawings, illustrating by way of example the principles of the described embodiments.

DETAILED DESCRIPTION

The described embodiments include methods, systems and apparatuses that monitor breathing of a user, and can additionally identify breathing patterns of the user. Both the breath rate and the identified breathing patterns can be used to monitor the general health of the user, and identify emergency situations.

Figure 1:
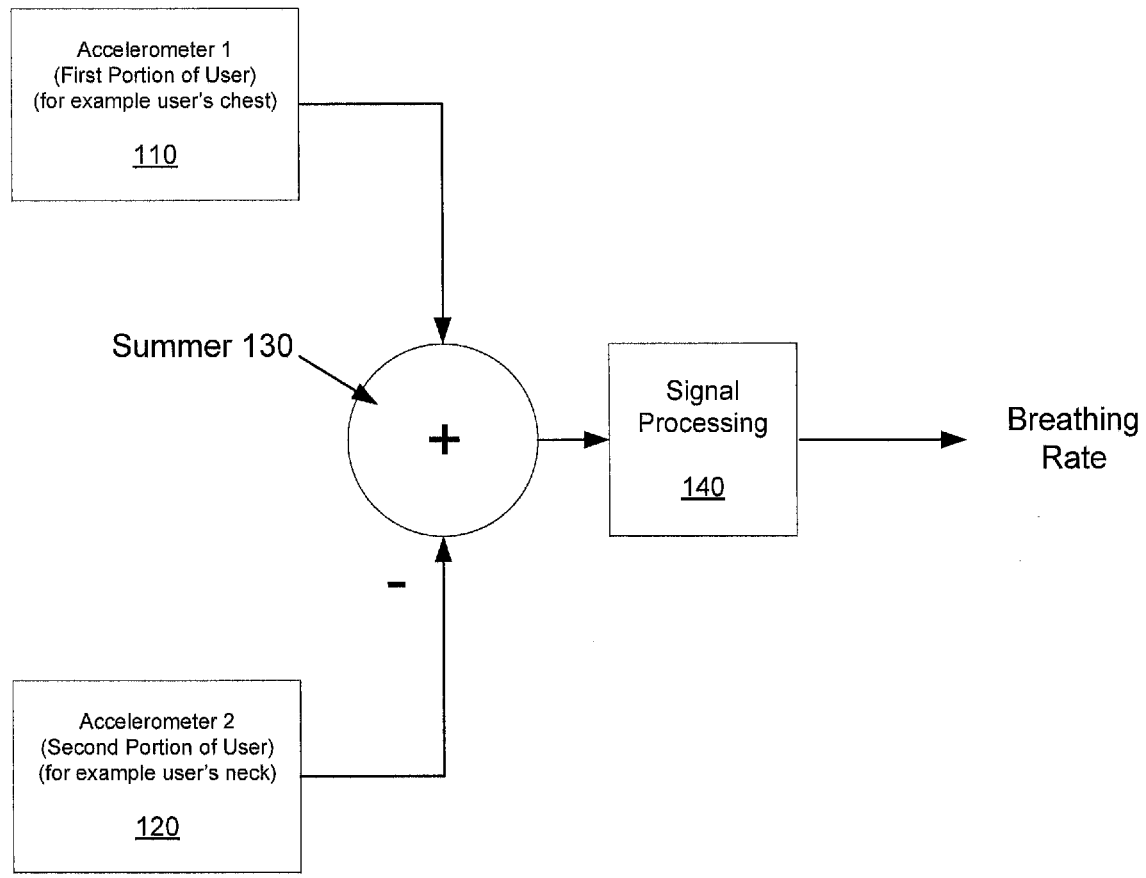
FIG. 1 shows an example of a block diagram of a breathing monitoring apparatus or system.

FIG. 1 shows an example of a block diagram of a breathing monitoring apparatus or system. The block diagram includes a first motion sensor 110 and a second motion sensor 120. By strategically placing the motion sensors 110, 120 on (proximate, ideally touching) a user, the breathing of the user can be monitored.

The human body generates many gross body movements, particularly when in motion (such as, walking, running and/or moving about). The motion of the body of the user created by a sensed breath signal is a weaker signal compared the signals generated by the gross body movements. The described embodiments provide for estimation of a breath signal by placing two motion sensors (such as, accelerometers) at two body locations where the effect of breath signal are essentially absent in one body location (for example, the neck of the user), while at the other location the sensed motion includes a combination of both body movements and breath (for example, the chest of the user).

That is, for example, the first motion sensor 110 is located at a first portion of the user (such as, at the user's chest) and the second motion sensor 120 is located at a second portion of the user (such as, at the user's neck). The sensed motion signal are inversely summed at a summer 130, thereby effectively cancelling the gross motions from the sensed signal, yielding a summed signal that ideally (of course the ideal situation is never realized as will be described) includes just the sensed breath signal.

Signal processing 140 of the summed signal yields the breathing rate of the user. As will be described, the signal processing 140 identifies periodic signals of the summed signal.

Figure 2:
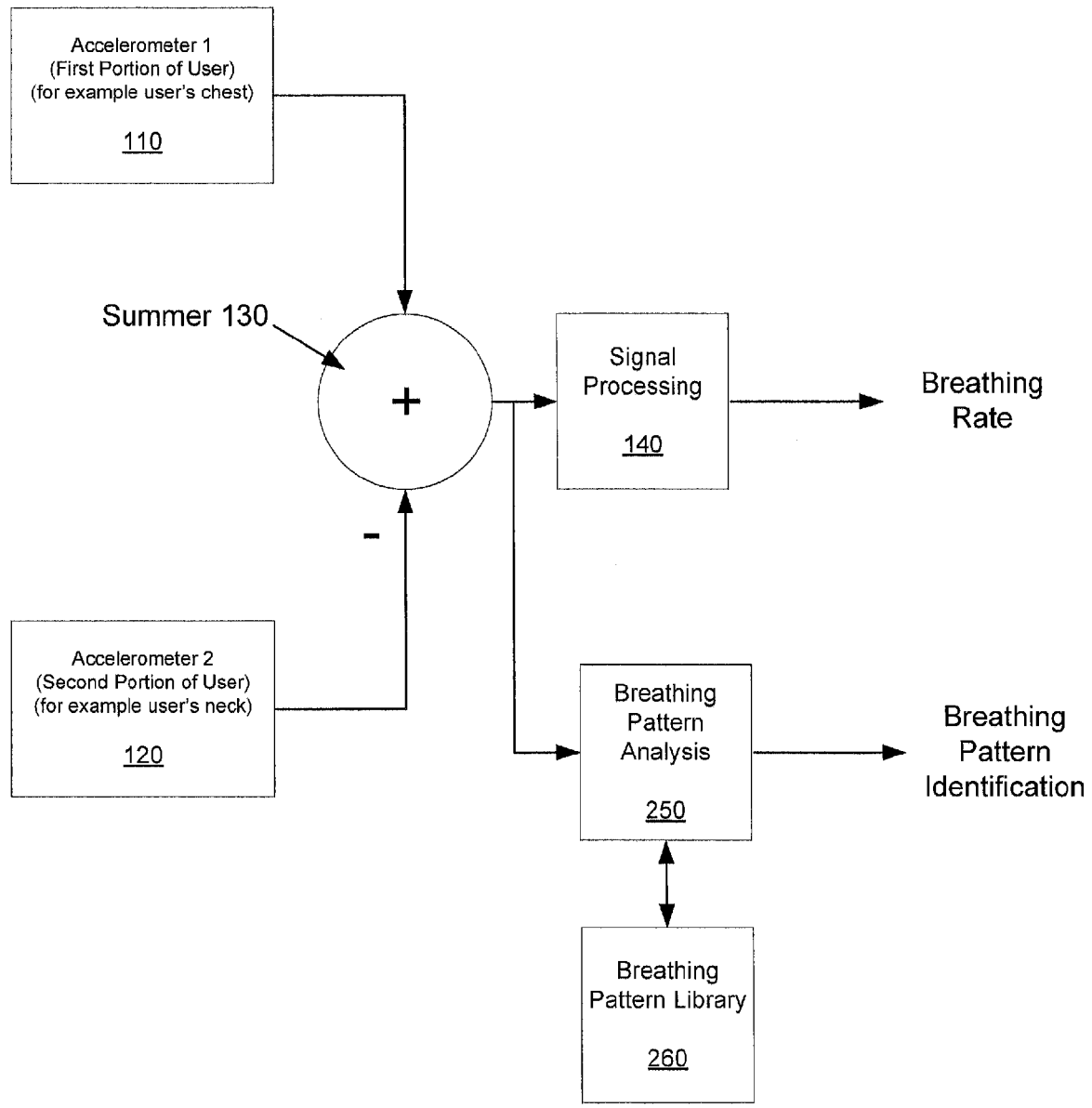
FIG. 2 shows an example of a block diagram of a breathing monitoring and breathing pattern recognition apparatus or system.

FIG. 2 shows an example of a block diagram of a breathing monitoring and breathing pattern recognition apparatus or system. FIG. 2 further includes breathing analysis. That is, breathing pattern analysis processing 250 monitors the sensed breathing signal (that is, the summed signal) over a period of time. The breathing pattern analysis processing 250 then compares the monitored breathing signal (which can be referred to as the breathing pattern signature) with, for example, a library of stored breathing pattern signatures. If a successful match is identified, then the breathing pattern of the user is identified. Note that the breathing pattern matching can be made in conjunction with an activity being performed by the user. The breathing pattern analysis can from time to time update the breathing pattern library with newer patterns and situations, once a new pattern has been identified.

Examples of useful breathing patterns that can be stored within the breathing pattern library include a breathing pattern corresponding to the user exhibiting deep breath, normal breath, a breathing pattern similar to stroke (uneasy) situation, and/or a breathing pattern for a breathless situation. Depending upon the breathing pattern of the user that is identified, an alert or other action can be initiated by the breathing monitoring and breathing pattern recognition apparatus or system. Embodiments of the breathing pattern library contain a tabulation of acceptable and unacceptable patterns for specified activity, stress and other conditions. This tabulation helps in accurately generate alerts.

Figure 3:
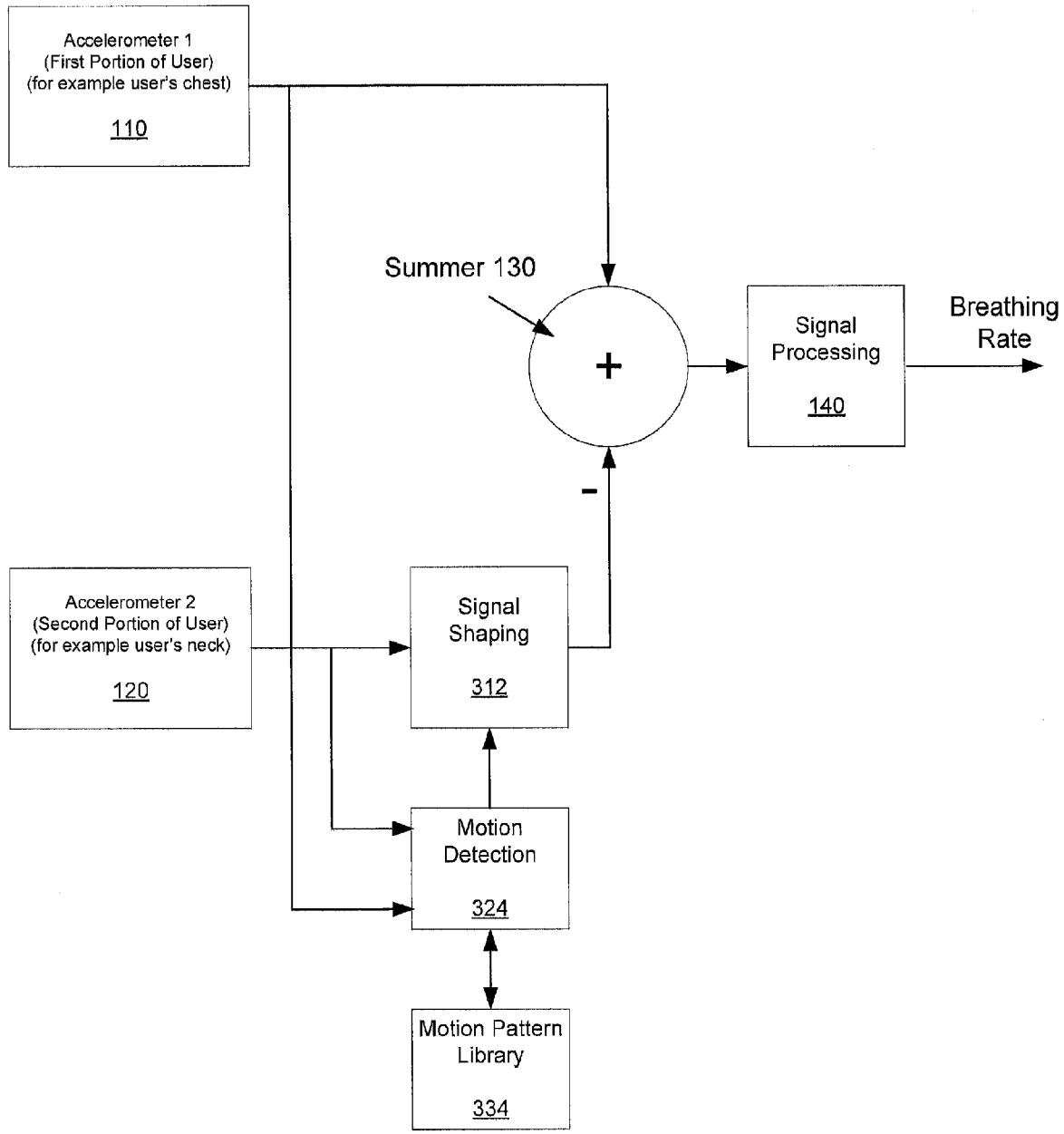
FIG. 3 shows another example of a block diagram of a motion monitoring apparatus or system.

FIG. 3 shows another example of a block diagram of a breathing monitoring apparatus or system. As previously mentioned, it is very difficult to completely cancel the gross motions from the summed signal. Therefore, some additional processing of at least one of the sense motion signals can be included to provide additional suppression of signal interference and/or noise due to the gross motions.

FIG. 3 additionally includes signal processing (signal shaping) 312 of the sensed motion signal of the second motion sensor 120. For this embodiment, the gross motion of the user is identified by matching signatures of the first and second motion sensors with stored motion (acceleration) signatures stored within a motion pattern library 334. That is, the library includes two or more stored motion signatures or patterns. By matching signatures (monitored motion signals over a period of time) the gross motion of the user can be identified. For example, the motion detection 324 can identify that the user, is, for example, sitting, walking, running or just fell down. Based on the motion detection, the sensed motion signal of the second sensor can be shaped to help eliminate the sensed gross motions of the user from the summed signal.

As will be described, current activity details (motion activity and the matched pattern) are fed to a re-estimator. Because of the context of the motion signatures, the re-estimator is able to guess initial guess values of new filter coefficients, using the matched motion details. Using the current acceleration signals at the first and second sensors, these coefficient values are then iteratively refined for generating the best estimation of second (chest) acceleration component from the first (neck) acceleration signal.

Figure 4:
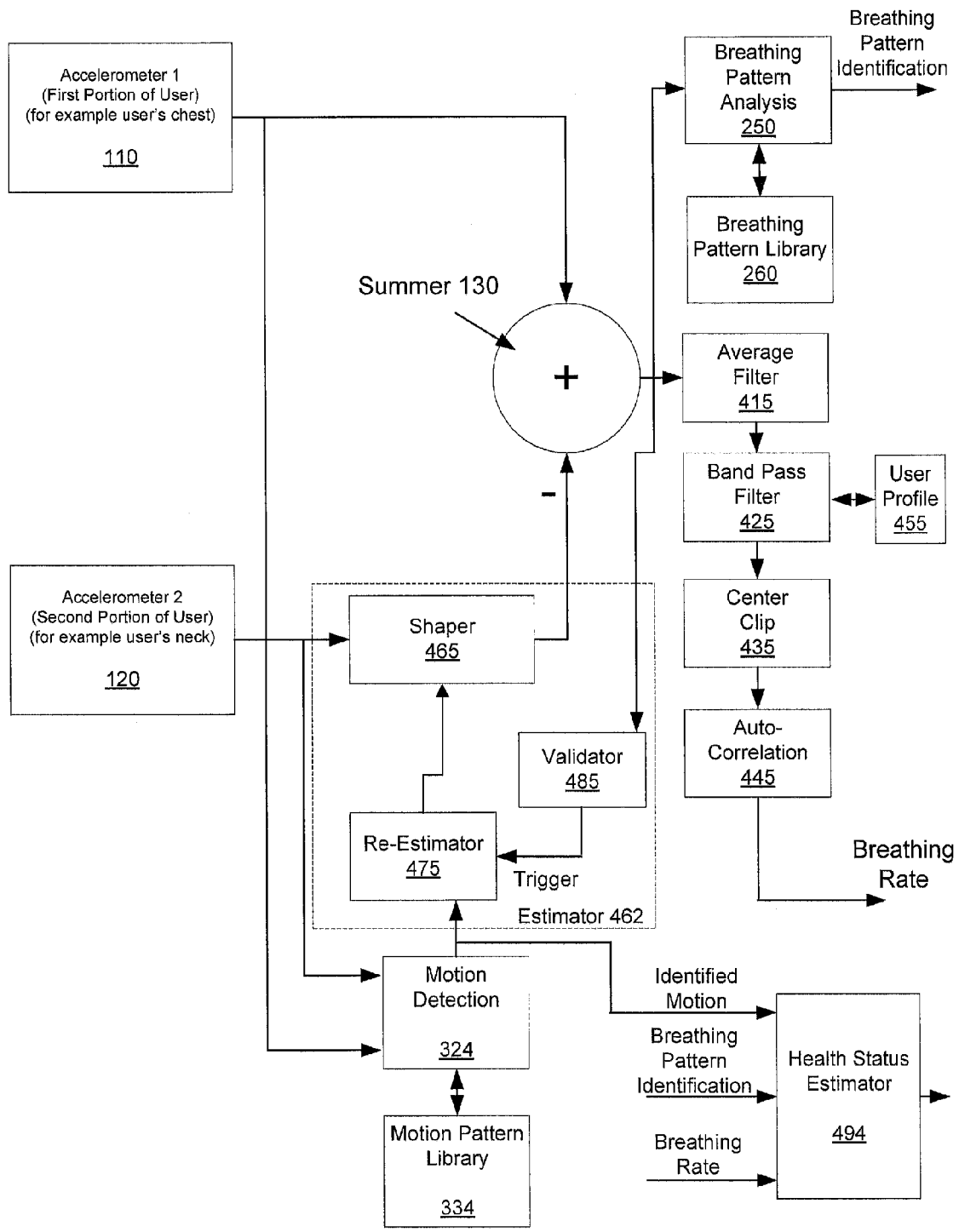
FIG. 4 shows another example of a block diagram of a breathing monitoring and breathing pattern recognition apparatus or system.

FIG. 4 shows another example of a block diagram of a breathing monitoring and breathing pattern recognition apparatus or system. The embodiment includes additional details of the signal processing of the sensed motion signals and additional details of signal processing of the summed signal.

Adaptive estimator circuitry 462 including a signal shaper 465, a re-estimator 475 and a validator 485, which provides processing to convert the sensed motion signal at neck into an equivalent matching signal at the chest due to body movement only. The signal shaper 465 includes a combination of gain blocks (FIR and IRR filters). The coefficients of the gain blocks are estimated (adjusted) to improve the conversion of the sensed motion signal at neck into an equivalent matching signal at the chest due to body movement only. After subtracting the sensed motion signal from original chest acceleration signal, the summed signal include a stronger breath acceleration component.

The validator block 485 monitors, for example, the summed signal at the output of the summer 130. When the filter model no longer remains valid, the output shoots up beyond breath signal expected amplitudes. This triggers the re-estimator block 475. Re-estimator block 475 computes the updated filter coefficients from the two acceleration input streams. The validator block 485 continuously monitors and validates the data coming from the summer 130 for summed signal. It monitors this signal to see if the estimated reconstructed signal generated from the signal shaper 465 is generating a correct signal based on current activity, coefficients, motion library and user profiles. If it determines that the estimated signals are not optimal, it sends a trigger to the re estimator block 475 to pick more appropriate parameters for the given condition so that the resulting signal from the summer 130 contains an accurate breath signal.

The motion detection 324 can identify motions of the user. The current activities as identified by the motions of the user can be input to the re-estimator 475. Because of the context of the motion signatures, the re-estimator 475 is able to guess new filter coefficients better, using the matched motion details. These coefficients are then iteratively refined for generating the best estimation of chest acceleration component from the neck acceleration signal.

The sensed motion (acceleration) signals of the first portion of the user (user's chest) and the second portion of the user (user's neck) contain a major signal that comes from the coherent (common) source (the body movement). However due to body physics, the signals are not exactly identical as sensed at any two locations on the body. Some frequency components may be dampened more while others may be boosted at a different body location, relative to each other. The estimator 462 adapts itself so that its filter parameters are adjusted to minimize the difference in the two signals. This can be achieved when the signal component at the chest due to body movement may be most accurately reconstructed. In such a case, the residual signal has dominant component that is generated due to the breathing movement.

The validator 485 is a time-series monitor. When the input to the validator 485 shows up more than X % samples greater than an absolute threshold, it returns FALSE. For a valid input, the output is TRUE. For a good match of model, the estimated breath signal will have its value less than the absolute threshold, with only occasional mismatch. But with an invalid model, the subtracted output has several values greater than the absolute threshold.

For the signal processing of the summed signal, an averaging filter 415 sums M consecutive samples of a time series of the summed signal, together, effectively averaging the summed signal. This enhances the low-frequency breath signal within the summed signal. The high-frequency noise is effectively reduced.

A band-pass filter 425 receives the averaged summed signal, and has a pass-band that is centered based on the breath rates typically found with the profile of the person. The profile can be stored, for example, within a user profile 455 which aids in tuning the band-pass filter 425. The band-pass filter 425 reduces noise and interfering signals.

A center clipper 435 additionally reduces noise within the summed signal.

An auto-correlator 445 auto-correlates the filtered and center clipped summed signal. A first positive peak of the auto-correlation is compared to a threshold value. If this is higher than the threshold, the breath rate is computed from the lag at the positive peak.

Autocorrelation is a cross-correlation of the signal with itself. A measure of the similarity between two different data sets, computed by the sum of the cross products between the two data sets at different lags (it is a function of the lag). Thus, if the signal has a periodicity, then the autocorrelation has a peak at a time delay that is multiple of the period. The first positive peak after zero time-lag is the period of the strong periodic component in the time series.

For embodiments, there are 3 signals (x, y, z) for each motion sensor (accelerometer). The three signals include three channels of data, which when sensed at the neck, are used to estimate the three components at the chest data. For this embodiment, the summer 130 also includes three channels (vector subtraction or summation). The gross body orientation decides the relative strength of breath signal in the channels. The strongest signal is selected for autocorrelation purpose.

A health estimator block 494 receives the identified motion of the user from the motion detection block 324, the breathing pattern identification and the breathing rate. The sensed motions states and the sensed breath patterns, and breath rate are further correlated to estimate the health status of the person. This can be a positive estimate—like the person does not get breathless while jogging or aerobic exercises. Alternatively or additionally, this includes health alerts, for example, when the person (user) feels breathless even during relatively light motion activity.

Figure 5:
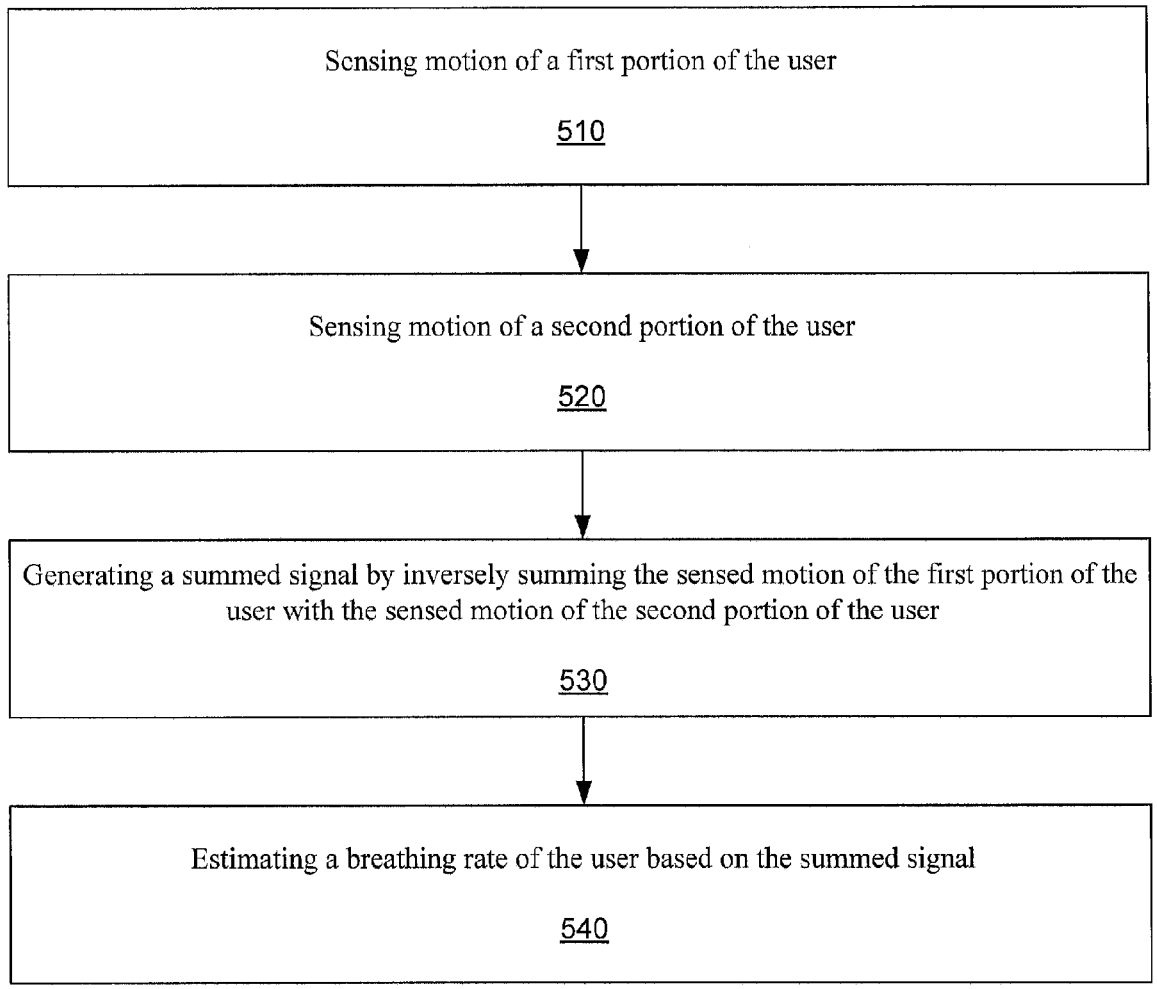
FIG. 5 is a flow chart that shows an example of steps of a method for analyzing breathing of a user.

FIG. 5 is a flow chart that shows an example of steps of a method for analyzing breathing of a user. A first step 510 includes sensing motion of a first portion of the user. A second step 520 includes sensing motion of a second portion of the user. A third step 530 includes generating a summed signal by inversely summing the sensed motion of the first portion of the user with the sensed motion of the second portion of the user. A fourth step 540 includes estimating a breathing rate of the user based on the summed signal.

Embodiments include estimating the breathing rate by identifying a periodic component of the summed signal. Embodiments include enhancing the periodic component within the summed signal by averaging, band-pass filtering and center clipping. Embodiments include the period of the enhanced output being measured by autocorrelation. The period is then inversed, and further multiplied by a time-scaling factor to provide a breath rate per desired time period (for example, breaths-per-minutes).

Embodiments include processing the summed signal to improve the sensed breath signal relative to noise and interference of the summed signal. Embodiments of the processing of the summed signal include averaging the summed signal, band-pass filtering the summed signal, optionally center-clipping the summed signal, and auto-correlating the summed signal.

An embodiment of center clipping is defined as a function of a value of a clipping limit (CL). An output y(n) of center clipping for an input x(n) can be defined as:

$$y(n)=x(n)-CL; \text{ if } x(n)>CL$$

$$y(n)=0; \text{ if } -CL<x(n)<CL$$

$$y(n)=x(n)+CL; \text{ if } x(n)<-CL.$$

For an embodiment, for a time series x(n), autocorrelation is a function of lag (j) for a time series x(n). First, a length N of the time series is obtained. Next, a copy of the time series is made. Next, the time series is shifted by j elements to right. Zeroes are added in the first j−1 locations. The autocorrelation (j) is computed as the sum of products of each element in the time series with the corresponding element of shifted series. The process is repeated for lags of desired range between 0 and n, where:

$$y(j)=\Sigma x(i)*x(i-j) \ldots \text{ for } 0<=i<=n$$

For an embodiment, sensing motion of the first portion of the user comprises an accelerometer sensing the first portion at a location of the user's body that senses minimal motion due to breathing of the user, such as, the user's neck or spine. Additionally, embodiments include sensing motion of the second portion of the user comprises an accelerometer sensing the second portion at a location of the user's body that senses motion due to breathing of the user, such as, the user's chest.

Embodiments further include identifying breathing patterns of the user. This includes generating a motion signature based on sensed motion of the summed signal, matching the motion signature with at least one of a plurality of stored motion and/or breathing signatures, wherein each stored acceleration signatures corresponds with a breathing pattern, and identifying a breathing pattern of the user based on the matching of the motion signature with the stored motion signature.

Embodiments include further processing the sensed motion of at least one of the sensed motion of the first portion of the user and the sensed motion of the second portion of the user based on the identified type of motion of the user. For embodiments, this includes generating a motion signature based on sensed motion of at least one of the sensed motion of the first portion of the user and the sensed motion of the second portion of the user, matching the motion signature with at least one of a plurality of stored motion signatures, wherein each stored motion signatures corresponds with a type of motion, identifying a type of motion of the user based on the matching of the motion signature with the stored motion signature, and selecting the processing of the sensed motion based at least in part on the identifying a type of motion of the user.

Figure 6:
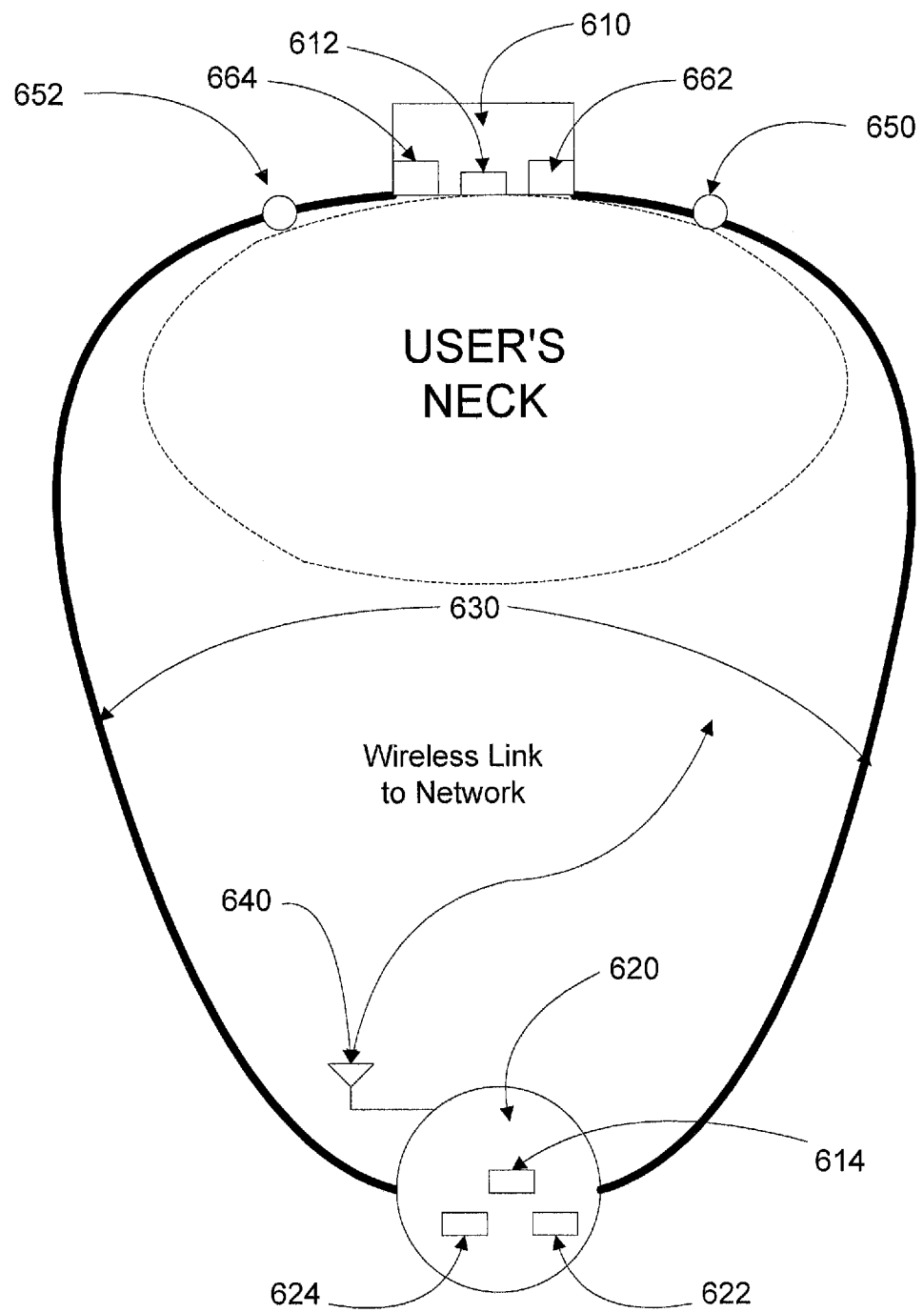
FIG. 6 shows an example of a wearable motion sensing device that utilizes embodiments of the breathing monitoring and/or breathing pattern recognition apparatus or system.

FIG. 6 shows an example of a wearable motion sensing device that utilizes embodiments of the breathing monitoring and/or breathing pattern recognition apparatus or system. This embodiment of the wearable motion sensing device includes a first motion sensor 610 and a second motion sensor 620. The second motion sensor 620 may be located within, for example, a pendant. An insulated conductor 630 provides an electrical connection between the first motion sensor 610 and the second motion sensor 620. When worn by, for example, a human being, the first motion sensor 610 can sense gross motion of the human being and the second motion sensor 620 can sense both gross motions and breathing motions. Electrical signals that represent the sensed motions can conduct through the insulated conductor 630.

The first motion sensor 610 can include an accelerometer 612, such as a tri-axial an accelerometer for generating an electrical signal based on motion of the first motion sensor 610. The second motion sensor 620 can include an accelerometer 614, such as a tri-axial an accelerometer for generating an electrical signal based on motion of the second motion sensor 620. For an embodiment, the second motion sensor 620 can include a processor 622 for receiving the electrical signals (at least a representation of the electrical signals) and performing processing to identify the sensed motions. In some cases, communications circuitry 624 of the second motion sensor 620 can be used to communicate the sensed motions to a network. The communications can be wireless, and transmitted and/or received by the second motion sensor through an antenna 640.

Additionally, the second motion sensor 620 can include a battery to power the processor 612 and the communications circuitry 624. Battery power can be provided to the first motion sensor 610 through the insulated conductor 630, or the first motion sensor 610 can include its own battery.

For an embodiment, the wearable motion sensing device can be worn like a necklace around a user's neck. The second motion sensor 620 can be attached to the wearable motion sensing device at a location of the wearable motion sensing device relative to the first motion sensor 610 that when worn by a human being, a mass of the second motion sensor 620 urges the first motion sensor 610 towards the human being. More specifically, the first motion sensor 610 is urged towards the human being's neck, thereby providing an accurate representation of motion of the human being's torso. For an embodiment, the first motion sensor 610 is attached to the necklace at a diametrically opposed location of the necklace as to where the second motion sensor 620 is attached to the necklace.

The described embodiments provide several advantageous features. An embodiment includes a necklace that has two parts. A first part is a clasp which when worn is located right behind the neck of the human wearing the necklace, and is typically in contact with the body. The second part includes the pendant (for example, the second motion sensor 620) hanging around the front of the neck or the chest. For an embodiment, the first motion sensor is embedded in the clasp of the necklace, whereas the pendant contains other electronics that are required for the sensor to operate (these could be the CPU, battery, flash, memory, wireless circuitry, beepers, and other ancillary circuitry). The clasp containing the first motion sensor is electrically connected to the pendant via the necklace chain, which contains wires to send electrical signals between the motion sensor and the pendant. These electrical leads are insulated, so that any other metal in the chain or contact with the human skin will not cause any electrical shorting or distortion of the electrical signal. The necklace may be designed to be ornamental, such that people would want to wear it, and there can be various styles of it suitable to women and men.

For embodiments, the clasp of the necklace is tiny and unobtrusive. The clasp is constantly in contact with the skin at the back of the neck. However, it can be acceptable to be behind the collar of a garment. The locket or pendant contains most of the remaining electronics of the motion sensing device, including the battery, CPU, wireless circuitry and more. Although the locket or pendant may swing around as the person is wearing the necklace, the clasp at the back of the neck will essentially be moving in direct concert with the movement of the person's torso, or more specifically the person's neck.

Several characteristics of the necklace lend themselves to accurate detection of motion around the clock. The necklace can essentially be worn continuously, and users (those who wear the necklace) do not need to take it on and off as they transition through their various daily activities. This makes accidental loss of the device less likely, as well as having the device land in an undesirable place such as a laundry basket or the floor. The first motion sensor 610 is typically in contact with the human skin, and as such its movements are directly those of the human torso. These movements are unfettered by any relative motions of the person's garments. The necklace motion sensor can be worn during a person's shower, and does not need to be removed when they are in the bathroom. The necklace can be made small and attractive, such that people would want to wear it. Any number of decorative styles is possible to suit different personal preferences.

The wearable motion sensing device can additionally include electrodes 650, 652 which are electrically connected to a conductor within the electrical conductor 630. Electrical signals of the electrodes 650, 652 can be coupled to electrocardiogram processing located, for example, in the second motion sensor 620. The electrodes 650, 652 are preferably located so that when the wearable motion sensing device is worn by a user, the electrodes 650, 652 physically contact the skin of the user, for example, the skin on the back of the user's neck. An embodiment includes the electrodes 650, 652 being collocated with the first motion sensor 610. An electrocardiogram (EKG or ECG) is a test that checks for problems with the electrical activity of your heart, and allows for determination of the user's heart rate rhythm. This embodiment provides an alternative to traditional chest wraps.

Additionally, as shown the first motion sensor 610 or clasp can additionally include a temperature sensor 662 and/or a moisture sensor 664. Similar to the electrodes, the temperature sensor 662 and the moisture sensor 664 are preferably in physical contact with the user's skin.

Figure 7:
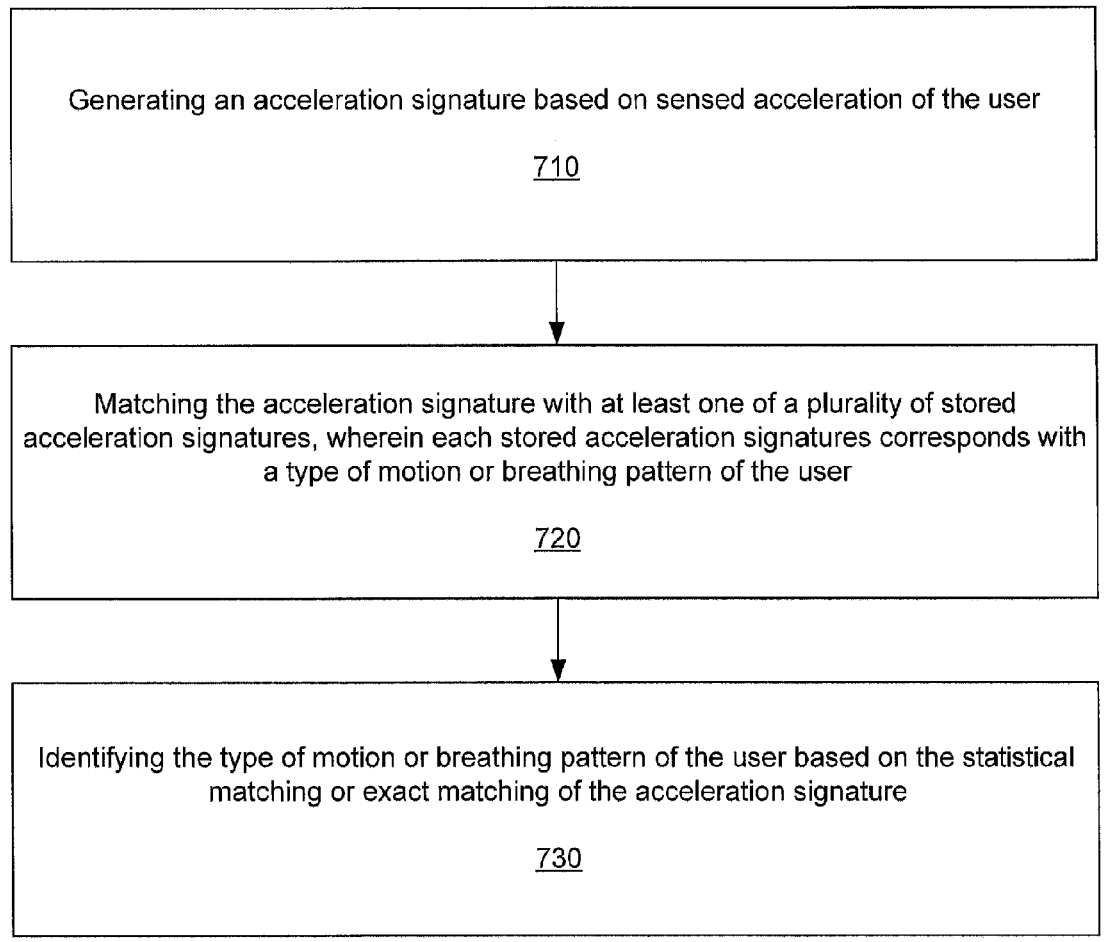
FIG. 7 is a flow chart that includes the steps of one example of a method of identifying a type of motion or breathing pattern of the user.

FIG. 7 is a flow chart that includes the steps of one example of a method of identifying a type of motion of the user. The motion can be a breathing pattern, and/or motion of the user. As previously described, the motion of the user can be used for processing of the sensed motion signals (FIG. 3 and FIG. 4) and for additionally estimating the health of the user (FIG. 4). A first step 710 includes generating an acceleration signature (for example, a tri-axial) based on the sensed acceleration of the user. A second step 720 includes matching the acceleration signature with at least one of a plurality of stored acceleration signatures, wherein each stored acceleration signatures corresponds with type of motion or breathing pattern. A third step 730 includes identifying the type of motion or breathing pattern of the user based on the statistical (pattern) matching or exact matching of the acceleration signature. The acceleration signal can be created using a wavelet transformation.

Though embodiments of generating matching acceleration signatures are described, it is to be understood that additional or alternate embodiments can include generating and matching of orientation and/or audio signatures. Correspondingly, the first step 710 can include generating an acceleration signature, (and/or) orientation and audio signature based on the sensed acceleration, orientation of the object and audio generated by the motion sensing device, for example, a thud of a fall, or a cry for help.

Elemental motion includes but is not limited to motion patterns for walking, running, fitness motions (for example, elliptical machine exercises, rowing, stair climbing, aerobics, skipping rope, bicycling . . . ), vehicular traversal, sleeping, sitting, crawling, turning over in bed, getting out of bed, getting up from chair, and more.

Macro-motion includes but is not limited to going for a walk in the park, leaving home and driving to the shopping center, getting out of bed and visiting the bathroom, performing household chores, playing a game of tennis, and more.

Each of the plurality of stored acceleration signatures corresponds with a particular type of motion. By matching the detected acceleration signature of the motion sensing device with at least one of a plurality of stored acceleration signatures, an estimate or educated guess can be made about the detected acceleration signature.

An embodiment includes a common library and a specific library, and matching the acceleration signature includes matching the acceleration signature with stored acceleration signatures of the common library, and then matching the acceleration signature with stored acceleration signatures of the specific library. For a particular embodiment, the general library includes universal acceleration signatures, and the specific library includes personal acceleration signatures. That is, for example, the stored acceleration signatures of the common library are useable for matching acceleration signatures of motions of multiple humans, and the stored acceleration signatures of the specific library are useable for matching acceleration signatures of motions of a particular human. Additionally, each library can be further categorized to reduce the number of possible matches. For example, at an initialization, a user may enter physical characteristics of the user, such as, age, sex and/or physical characteristics (such as, the user has a limp). Thereby, the possible signatures matches within the general library can be reduced. The signature entries within the specific library can be learned (built) over time as the human wearing the motion detection device goes through normal activities of the specific human. The specific library can be added to, and improved over time.

An embodiment includes filtering the acceleration signals. Additional embodiment include reducing the number of stored acceleration signature matches by identifying a previous activity of the motion sensing device, and performing a time domain analysis on the filtered acceleration signal to identify transient signatures or steady-state signatures of the filtered acceleration signal. That is, by identifying a previous activity (for example, a human walking of sleeping) the possible number of present activities can be reduced, and therefore, the number of possible stored acceleration signature matches reduced. Additionally, the transient and/or steady-state signatures can be used to reduce the number of possible stored acceleration signature matches, which can improve the processing speed.

An embodiment includes the stored acceleration signatures corresponding with different types of motion related to the person (user). A particular embodiment includes identifying an activity of the person based on a sequence of identified motions of the person. The activity of the person can include, for example, falling (the most important in some applications), walking, running, driving and more. Furthermore, the activities can be classified as daily living activities such as walking, running, sitting, sleeping, driving, climbing stairs, and more, or sporadic activities, such as falling, having a car collision, having a seizure and so on.

An embodiment includes transmitting information related to the identified type of motion if matches are made with particular stored acceleration signatures. The information related to the identified type of motion can include at least one of motions associated with a person the motion sensing device is associated with. The motions can include, for example, a heartbeat of the person, muscular spasms, facial twitches, involuntary reflex movements which can be sensed by, for example, an accelerometer. Additionally, the information related to the identified type of motion can include at least one of location of the motion sensing device, audio sensed by the motion sensing device, temperature of the motion sensing device.

Another embodiment includes storing at least one of the plurality of stored acceleration signatures during an initialization cycle. The initializing cycle can be influenced based on what the motion sensing device is attached to. That is, initializing the stored acceleration signatures (motion patterns) can be based on what the motion sensing device is attached to, which can both reduce the number of signatures required to be stored within, for example, the general library, and reduce the number of possible matches and reduce the processing required to identify a match. Alternatively or additionally, initializing the stored acceleration signatures can be based on who the motion sensing device is attached to, which can influence the specific library. The initialization can be used to determine motions unique, for example, to an individual. For example, a unique motion can be identified for a person who walks with a limp, and the device can be initialized with motion patterns of the person walking with a limp.

An embodiment includes initiating a low-power sleep mode of the motion sensing device if sensed acceleration is below a threshold for a predetermined amount of time. That is, if, for example, a person is sensed to be sleeping, power can be saved by de-activating at least a portion of the motion sensing device.

Various methods can be used for sequence and/or signature matching. For example, one embodiment includes formation of macro motion signatures. The macro motion signatures are built from an output of state analysis vectors using known wavelet transformation techniques (for example, a Haar Transform). The transform performs pattern matching on current motion pattern with existing motion pattern library using, for example, DWT (Discreet Wavelet Transform) techniques. Complex motion wavelets are later matched using statistical pattern matching techniques, such as, HHMM (Hidden Heuristic Markov Model). The statistical pattern matching includes detecting and classifying events of interest. The events of interest are built by observing various motions and orientation states data of the motion sensing device. This data is used to train the statistical model which performs the motion/activity detection. Each activity has its own model trained based on the observed data. Embodiments can further include a learning system providing the right model for the user from a set of model. The learning system can aid in building newer (personal) patterns which are not in the library for the person who is wearing the motion detection device. Embodiments further include pre-building a motion database of motion libraries against which motion signatures are compared. The database adds new motion/states signature dynamically as they are identified.

Just as the handwritten signatures of a given human being are substantively similar from one signature instance to the next, yet have minor deviations with each new instance, so too will the motion signatures of a given human be substantively similar from one motion instance to the next, yet have minor deviations.

Algorithms used for pattern recognition (signature matching) should have the sophistication to accurately handle a wide range of motions. Such algorithms should have the ability to recognize the identical characteristics of a particular motion by a given human being, yet allow for minor variations arising from human randomness. Additionally, the devices used to monitor peoples' movement need to be miniature and easy to wear. These two objectives are fundamentally opposed. However, the described embodiments provide a single cohesive device and system that is both sophisticated enough to detect a wide range of motions.

Figure 8:
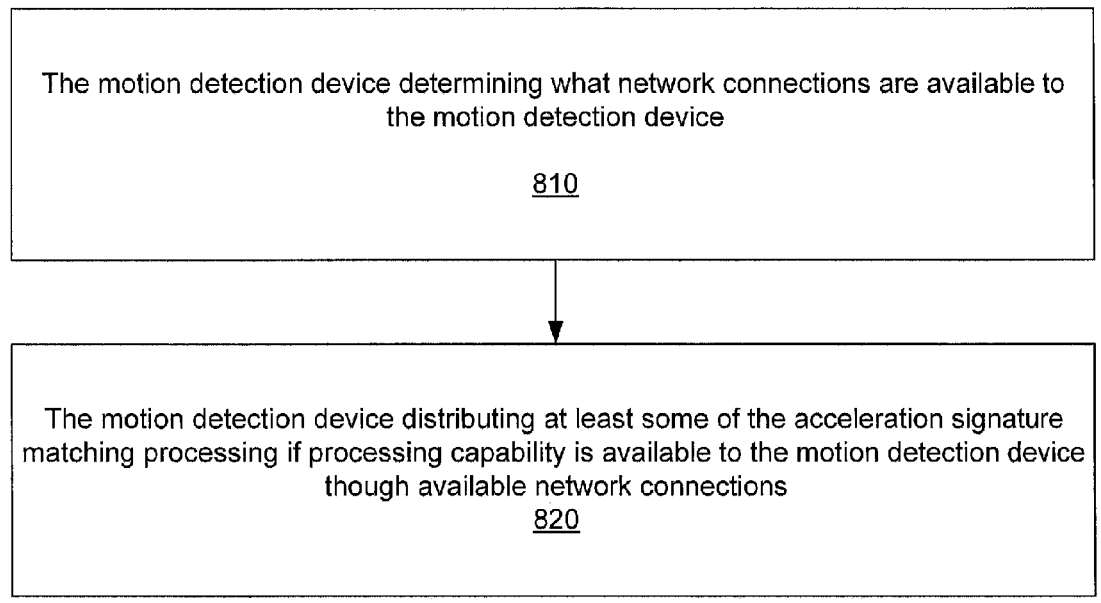
FIG. 8 is a flow chart that includes steps of one example of a method of a motion and breathing pattern detection device checking network availability for improvements in speed and/or processing power of acceleration signature matching.

FIG. 8 is a flow chart that includes steps of one example of a method of a motion detection/breathing monitoring device checking network availability for improvements in speed and/or processing power of acceleration signature matching, wherein the motion detection device includes motion detection sensors that generate the acceleration signal. A first step 810 includes the motion detection device determining what network connections are available to the motion detection device. A second step 820 includes the motion detection device distributing at least some of the acceleration signature matching processing if processing capability is available to the motion detection device though available network connections.

For an embodiment, the motion detection device distributes the acceleration signature matching processing if the processing capability is available to the motion detection device though available network connections, and distributing the acceleration signature matching processing saves the motion detection device processing power. Another embodiment, the motion detection device distributes the acceleration signature matching processing if the processing capability is available to the motion detection device though available network connections, and distributing the acceleration signature matching processing increases a speed of the motion detection device processing. Alternatively, the motion detection device distributes the processing to optimize both power and processing speed. Additionally, the processing distribution can be dependent upon the bandwidths of the available network connections. That is, some networks connections can generally support higher data transfer rates, and therefore, influence the processing speed.

Generally, the motion detection device scales its processing to the level of processing available. That is, as additional processing power becomes available to the motion detection device, the motion detection device can increase the complexity of the signature matching processing. The processing can be distributed as processing capability becomes available through network connections. The processing can be performed in different locations as network connectivity becomes available, which can advantageously reduce the power consumption of the motion detection device and/or increase the speed of the processing.

Figure 9:
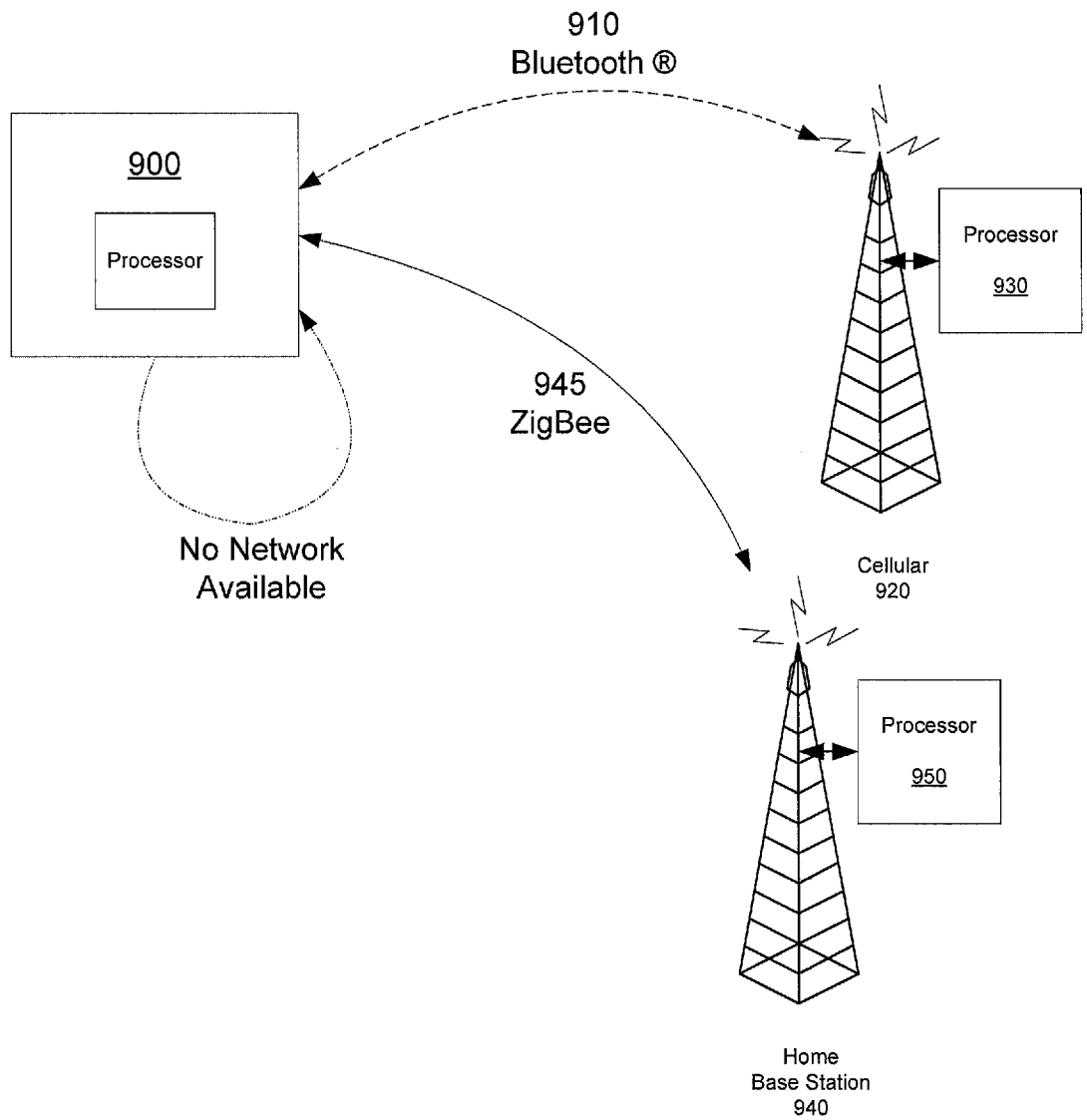
FIG. 9 shows an example of at least one of a breathing monitoring and/or motion detection and tracking device that can be connected to one of multiple networks.

FIG. 9 shows a motion detection/breathing monitoring device 900 that can be connected to one of multiple networks. Examples of possible networks (not a comprehensive list) the motion detection device 900 can connect to, include a cellular network 920 through, for example, a Bluetooth wireless link 910, or to a home base station 940 through, for example, a Zigbee wireless link 945. The wireless links 910, 945 can each provide different levels of bandwidth. Each of the networks includes available processing capabilities 930, 950.

If the motion detection/breathing monitoring device 900 does not have any network connections available, the motion detection/breathing monitoring device 900 must perform its own matching processing and breathing monitoring. If this is the case, then the processing algorithms may be less complex to reduce processing power, and/or reduce processing speed. For example, the matching processing can be made simpler by comparing threshold levels for elemental motions by extracting significant wavelet coefficients. Acceleration signals data acquisition is performed in chunk of processing every few mili-seconds by waking up. For all other times the processor rests in low-power mode. Except for the emergency situation, the RF communication is done periodically when the data is in steady state, there is no need to send it to network i.e. when the motion sensing device is in sedentary there is no need to send data change in the state is communicated to network. Additionally, if no network connections are available, the operation of the motion detection/breathing monitoring device 900 may be altered. For example, if the motion detection/breathing monitoring device 900 detects an emergency situation (such as, a fall), the motion detection device 900 can generate an audio alert. If a network connection was available, the audio alert may not be generated, but an alert may be transmitted over the available network.

The motion detection/breathing monitoring device 900 includes a controller in which at least a portion of the analysis and signature matching can processing can be completed. However, if the motion detection/breathing monitoring device 900 has one or more networks available to the motion detection/breathing monitoring device 900, the motion detection device can off-load some of the processing to one of the processors 930, 950 associated with the networks. The processing required for identification of motion, activity, behavior, and/or behavior patterns can all be distributed across the network as selected.

The determination of whether to off-load the processing can be based on both the processing capabilities provided by available networks, and the data rates (bandwidth) provided by each of the available networks.

FIGS. 10A, 10B, 10C, 10D show examples of different types of breathing patterns for human beings. It should be noted that these signatures are expected to have certain components that are common from one human being to the next, but also have certain components that vary from one human to the next.

Figure 10A:
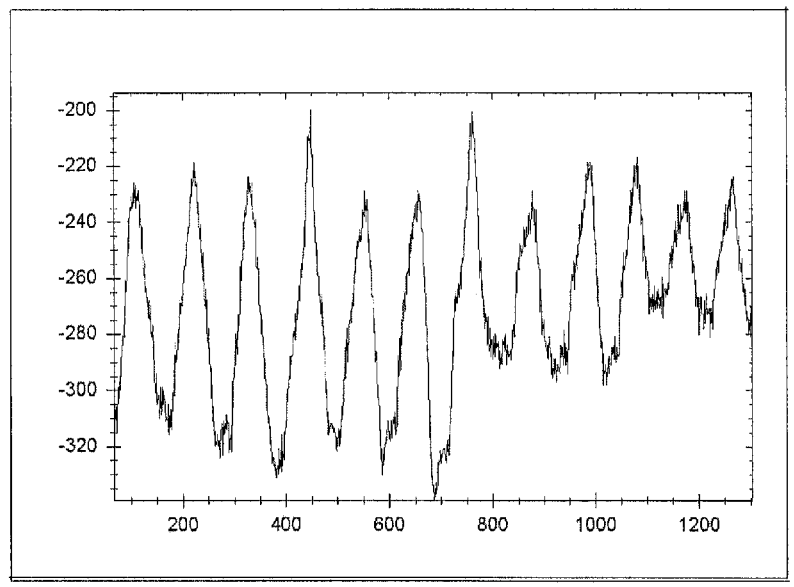
FIGS. 10A, 10B, 10C, and 10D show examples of typical breathing patterns.
Figure 10B:
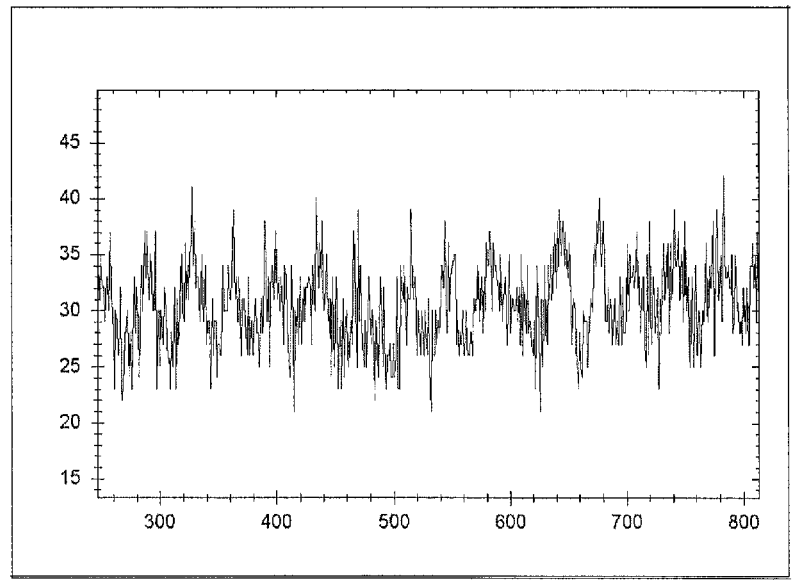
Figure 10C:
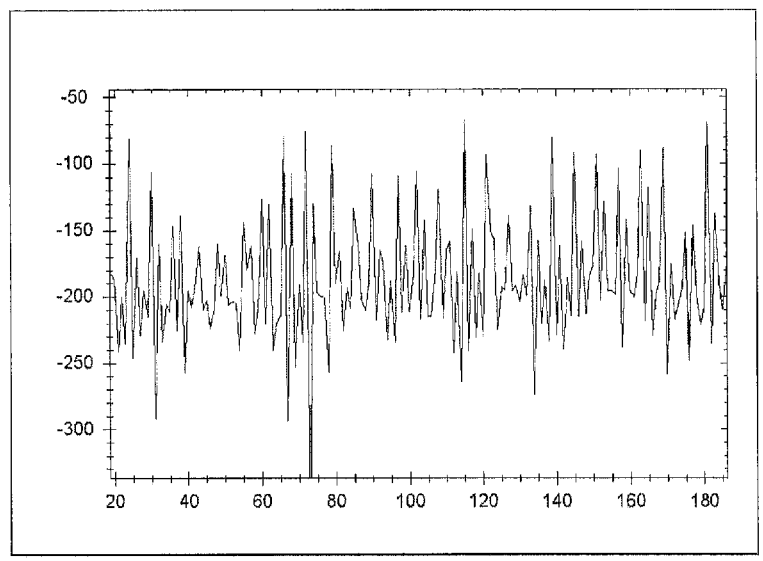
Figure 10D:
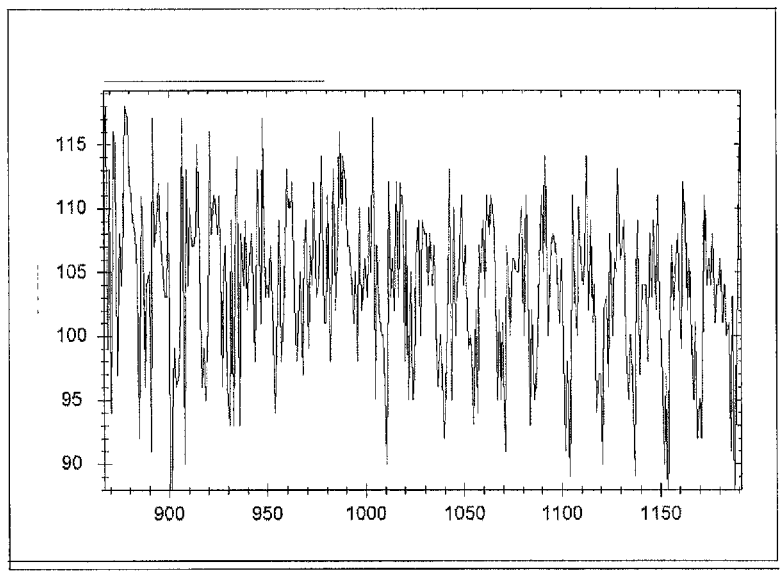

FIG. 10A shows an example of a breathing pattern for deep breathing. FIG. 10B shows an example of breathing pattern for normal breathing. FIG. 10C shows an example of a breathing pattern for a slow inhale and a fast exhale. FIG. 10D shows an example of a breathing pattern for shortness of breath as a result of an aerobic activity. By matching a sensed breathing signature that has been generated by sensing the motion of a person with one of many stored breathing pattern signatures, the breathing pattern of the person can be determined. As described, the health of the person (user) can be estimated based at least in part on the identified breathing pattern.

Although specific embodiments have been described and illustrated, the embodiments are not to be limited to the specific forms or arrangements of parts so described and illustrated.

What is claimed:

1. A method for analyzing breathing of a user, comprising:
    generating a first motion signal, comprising sensing motion, by a first motion sensor, of a first portion of a body of the user;
    generating a second motion signal, comprising sensing motion, by a second motion sensor, of a second portion of the body of the user;
    generating a summed signal by inversely summing the first motion signal and the second motion signal;
    estimating a breathing rate of the user based on the summed signal comprising identifying a periodic component of the summed signal;
    identifying a breathing pattern of the user, comprising:
        generating a motion signature based on sensed motion of the summed signal;
        matching the motion signature with at least one of a plurality of stored motion signatures, wherein each stored acceleration signatures corresponds with a breathing pattern;
        identifying the breathing pattern of the user based on the matching of the motion signature with the stored motion signature.

2. The method of claim 1, further comprising enhancing the periodic component within the summed signal by averaging, band-pass filtering and center clipping the summed signal.

3. The method of claim 1, further comprising measuring a period of the summed signal by auto-correlating the summed signal.

4. The method of claim 3, further comprising multiplying the auto-correlated summed signal with a time-scaling factor to provide a breath rate per desired time period.

5. The method of claim 1, further comprising signal processing the summed signal.

6. The method of claim 5, wherein the signal processing comprises filtering the summed signal.

7. The method of claim 5, wherein the signal processing comprises center-clipping the summed signal.

8. The method of claim 5, wherein the signal processing comprises auto-correlating the summed signal.

9. The method of claim 1, wherein sensing motion of the first portion of the user comprises an accelerometer sensing the first portion at a location of the user's body that senses minimal motion due to breathing of the user.

10. The method of claim 1, wherein sensing motion of the second portion of the user comprises an accelerometer sensing the second portion at a location of the user's body that senses motion due to breathing of the user.

11. The method of claim 10, wherein the first portion is located proximate to the user's spine or neck.

12. A method for analyzing breathing of a user, comprising:
    generating a first motion signal, comprising sensing motion, by a first motion sensor, of a first portion of a body of the user;
    generating a second motion signal, comprising sensing motion, by a second motion sensor, of a second portion of the body of the user;
    generating a summed signal by inversely summing the first motion signal and the second motion signal;
    generating a motion signature based on sensed motion of at least one of the sensed motion of the first portion of the user and the sensed motion of the second portion of the user;
    matching the motion signature with at least one of a plurality of stored motion signatures, wherein each stored motion signatures corresponds with a type of motion;
    identifying a type of motion of the user based on the matching of the motion signature with the stored motion signature.

13. The method of claim 12, further comprising selecting signal processing of the sensed motion of at least one of the sensed motion of the first portion of the user and the sensed motion of the second portion of the user based on the identified type of motion of the user.

14. A system for analyzing breathing of a user, comprising:
    a first sensor generating a first motion signal, comprising, sensing motion of a first portion of a body of the user;
    a second sensor generating a second motion signal, comprising sensing motion of a second portion of the body of the user;
    a summer operative to generate a summed signal by inversely summing the first motion signal and the second motion signal;
    processing circuitry operative to estimate a breathing rate of the user based on the summed signal comprising identifying a periodic component of the summed signal;
    a breathing analysis processor operative to:
        generate a motion signature based on sensed motion of the summed signal;
        match the motion signature with at least one of a plurality of stored motion signatures, wherein each stored acceleration signatures corresponds with a breathing pattern;
        identify a breathing pattern of the user based on the matching of the motion signature with the stored motion signature.

15. The system of claim 14, further comprising means for enhancing a periodic component within the summed signal by averaging, band-pass filtering and center clipping the summed signal.

16. The system of claim 14, further comprising an auto-correlator for measuring a period of the summed signal by auto-correlating the summed signal.

17. The system of claim 14, further comprising a filter operative to filter the summed signal.

18. The system of claim 14, further comprising means for center-clipping the summed signal.

19. The system of claim 14, further comprising means for auto-correlating the summed signal.

20. The system of claim 14, wherein the first sensor comprises an accelerometer sensing the first portion at a location of the user's body that senses minimal motion due to breathing of the user.

21. The system of claim 14, wherein second sensor comprises an accelerometer sensing the second portion at a location of the user's body that senses motion due to breathing of the user.

22. The system of claim 21, wherein the second portion is located proximate to the user's spine or neck.

23. An apparatus for analyzing breathing of a user, comprising:
- a first sensor generating a first motion signal, comprising, sensing motion of a first portion of a body of the user;
- a second sensor generating a second motion signal, comprising sensing motion of a second portion of the body of the user;
- a summer operative to generate a summed signal by inversely summing the first motion signal and the second motion signal;
- processing circuitry operative to estimate a breathing rate of the user based on the summed signal comprising identifying a periodic component of the summed signal;
- a processor operative to:
    - generate a motion signature based on sensed motion of at least one of the sensed motion of the first portion of the user and the sensed motion of the second portion of the user;
    - match the motion signature with at least one of a plurality of stored motion signatures, wherein each stored motion signatures corresponds with a type of motion;
    - identify a type of motion of the user based on the matching of the motion signature with the stored motion signature.

24. The apparatus of claim 23, wherein the processor is further operative to select signal processing of the sensed motion of at least one of the sensed motion of the first portion of the user and the sensed motion of the second portion of the user based on the identified type of motion of the user.

* * * * *